US006168769B1

(12) United States Patent
Zisman et al.

(10) Patent No.: US 6,168,769 B1
(45) Date of Patent: Jan. 2, 2001

(54) OLEFIN PURIFICATION

(75) Inventors: Stan A. Zisman; Kerry L. Evans, both of Bartlesville, OK (US)

(73) Assignee: Phillips Petroleum Company, Bartlesville, OK (US)

(*) Notice: Under 35 U.S.C. 154(b), the term of this patent shall be extended for 0 days.

(21) Appl. No.: 08/162,241

(22) Filed: Dec. 6, 1993

(51) Int. Cl.[7] .................................................. C07C 7/00
(52) U.S. Cl. ........................... 423/230; 95/139; 502/411; 585/824; 585/854
(58) Field of Search ........................... 423/230; 585/824, 585/854; 252/192; 95/139; 502/411

(56) References Cited

U.S. PATENT DOCUMENTS

| 1,441,696 | * | 1/1923 | McNeil ................................. 252/192 |
| 1,982,223 | | 11/1934 | Metzger et al. ........................ 23/150 |
| 2,470,214 | * | 5/1949 | Egan ..................................... 252/192 |
| 3,000,988 | * | 9/1961 | Karchmer et al. .................... 585/824 |
| 3,078,637 | | 2/1963 | Milton ..................................... 55/68 |
| 3,141,729 | | 7/1964 | Clarke et al. ............................ 23/4 |
| 3,517,484 | | 6/1970 | Lee et al. ................................ 55/73 |
| 3,619,130 | | 11/1971 | Ventriglio et al. ........................ 23/25 |
| 3,623,993 | * | 11/1971 | Pearson ................................ 423/625 |
| 3,865,924 | * | 2/1975 | Gidaspow ............................. 423/230 |
| 3,867,113 | | 2/1975 | Foster et al. ............................ 55/44 |
| 3,880,618 | | 4/1975 | McCrea et al. .......................... 55/68 |
| 3,885,927 | | 5/1975 | Sherman et al. ........................ 55/68 |
| 3,943,226 | | 3/1976 | Difford ................................ 423/230 |
| 4,039,620 | | 8/1977 | Netteland et al. .................... 423/230 |
| 4,433,981 | * | 2/1984 | Slaugh et al. ........................... 95/139 |
| 4,493,715 | | 1/1985 | Hogan et al. ............................ 55/68 |
| 4,835,338 | * | 5/1989 | Liu ....................................... 585/824 |
| 4,937,059 | * | 6/1990 | Kolts et al. ........................... 423/230 |
| 5,077,261 | * | 12/1991 | Schubert ............................... 423/230 |
| 5,302,771 | * | 4/1994 | Venkatram et al. .................. 585/823 |

FOREIGN PATENT DOCUMENTS

| 2194523 | * | 3/1988 | (GB) . |
| 2267096 | * | 11 1993 | (GB) . |
| 92/17428 | * | 10/1992 | (WO) . |

OTHER PUBLICATIONS

"Sofnolime RG", From Trade Journal "Hydrocarbon Processing", Apr. 1992 (No Page Given).*
Kirk–Othmer Encycl. Chem. Technol., vol. 2, pp. 492–493 (1978).
Kirk–Othmer Encycl. Chem. Technol., vol. 4, pp. 730–736 (1978).

* cited by examiner

Primary Examiner—Steven P. Griffin
Assistant Examiner—Timothy C Vanoy
(74) Attorney, Agent, or Firm—Richmond, Hitchcock, Fish & Dollar

(57) ABSTRACT

A process for purifying a fluid stream contaminated with carbon dioxide is provided which comprises contacting, under conditions sufficient to substantially remove the contaminated carbon dioxide from the fluid stream which contains at least one $C_2$–$C_5$ olefin such as ethylene or propylene, with A mixture containing an oxygen-containing metal compound such as, for example, an alkali metal hydroxide, and an inorganic oxide compound such as, for example, silica or alumina.

23 Claims, No Drawings

OLEFIN PURIFICATION

FIELD OF THE INVENTION

The present invention relates to a process for substantially removing carbon dioxide from a fluid containing at least one olefin where the fluid is contaminated with carbon dioxide.

BACKGROUND OF THE INVENTION

Olefin is a class of industrial chemicals useful as, for example, monomers or comonomers for the synthesis of polyolefins. However, the olefin must be substantially pure when it is used for synthesizing polyolefin, especially when the polyolefin is prepared in the presence of a high activity catalyst because any appreciable concentration of impurities can be detrimental to the catalyst. One of the impurities is carbon dioxide, a well-known catalyst inhibitor.

Alumina is a well known adsorbent in many chemical processes such as the polymerization of olefins, e.g. ethylene, for the removal of water and small concentrations of methanol, carbonyl-containing compounds, and peroxides. However, the use of alumina has disadvantages that impair its effectiveness as an adsorbent. For example, alumina has a low capacity when used as an adsorbent for the removal of $CO_2$ from an olefin fluid stream which contains $CO_2$ at low level concentrations and alumina must be regenerated when it becomes saturated with $CO_2$. Incurred regeneration costs over time dramatically impact the economics of its use.

Molecular sieves are frequently used as adsorbents for $CO_2$, but are inefficient when used for the removal of $CO_2$ from a fluid stream containing low molecular weight olefins such as ethylene.

Caustic scrubbers or bulk caustic scrubbers can also function as absorbents for $CO_2$ from a gaseous stream but have the disadvantages of being hazardous, and subject to water attack with subsequent caking thus severely limiting their capacity. It is therefore an increasing need to develop a more efficient process which is capable of reducing the carbon dioxide concentration in a fluid which contains an olefin to such levels that the $CO_2$ is not detrimental to catalyst activity in polymerization processes using the olefin.

SUMMARY OF THE INVENTION

An object of the present invention is to develop a composition for use in adsorbing carbon dioxide. Another object of the invention is to provide a process for removing carbon dioxide from a fluid stream employing the composition. An advantage of the present invention is that the composition provides a high loading capacity for adsorbing carbon dioxide. Other objects, advantages, and features will become more apparent as the invention is more fully disclosed hereinbelow.

According to the present invention, a process for removing carbon dioxide is provided which comprises contacting a fluid with a composition which comprises an oxygen-containing metal compound and an inorganic oxide compound wherein the fluid can be a gas stream, or a liquid stream, or both, and contains at least one $C_2$–$C_6$ olefin and carbon dioxide. The process is generally carried out under conditions sufficient to remove the carbon dioxide from the fluid and the composition is present in an effective amount to substantially remove the carbon dioxide from the fluid.

DETAILED DESCRIPTION OF THE INVENTION

According to the present invention, a fluid stream containing at least one $C_2$–$C_5$ olefin and a contaminated amount of carbon dioxide is contacted with a composition containing at least one oxygen-containing metal compound and an inorganic oxide. The olefin can be a normal or a branched olefin. The double bond can be at any position in the molecule. Examples of suitable olefins include ethylene, propylene, 1-butene, 2-butene, 2-methyl-1-butene, 1-pentene, 2-pentene, 3-methyl-1-butene, 4-methyl-1-pentene, and combinations of two ore more thereof. The presently preferred olefin is ethylene, or propylene, or both.

The oxygen-containing metal compound is generally an alkali metal compound or an alkaline earth metal compound including an alkali metal oxide, an alkali metal hydroxide, an alkaline earth metal oxide, an alkaline earth metal hydroxide, and combinations of two or more thereof. Examples of suitable oxygen-containing metal compounds include, but are not limited to, sodium oxide, sodium hydroxide, potassium oxide, potassium hydroxide, calcium oxide, calcium hydroxide, magnesium oxide, magnesium hydroxide, and combinations of two or more thereof. The presently preferred oxygen-containing metal compound is sodium hydroxide because of its ready availability and low cost.

According to the present invention, the inorganic oxide is generally the oxide used for catalyst support and is selected from the group consisting of silica, alumina, and combinations thereof. The silica employed in the invention can be any silica known in the art. The alumina employed in the invention can also be any alumina known in the art such as α, β, or δ-alumina.

The inorganic oxide employed generally can contain certain amount of impurities such as sodium oxide, ferric oxide, titanium oxide, and a metal sulfate.

The weight ratio of the oxygen-containing metal compound to the inorganic oxide can vary widely from as low as 0.01:1 to 10:1. Presently it is preferred that the weight ratio be in the range of from about 0.06:1 to about 9:1. The ratio is more preferably in the range of about 0.1:1 to about 5:1, and most preferably in the range of 0.15:1 to 4:1.

Generally the amount of the carbon dioxide sorbent composition used can vary widely depending on the concentration of carbon dioxide in the fluid stream to be removed as well as on the total quantity of the fluid to be treated and is an effective amount to substantially remove the carbon dioxide from the fluid. According to the present invention, the weight ratio of the carbon dioxide to the olefin is generally in the range of from about 0.000001:1 to about 0.1:1, some times 0.00001:1 to 0.01:1. Based on the contamination level of carbon dioxide in the fluid, as just described, the amount of the adsorbent required is dependent on the concentration of contaminating $CO_2$ in the fluid and is an effective amount for substantially removing the $CO_2$. It generally can be in the range of from about 1 to about 20 g, preferably about 2 to about 10 g, and most preferably 2 to 5 g of the oxygen-containing metal compound per g of the $CO_2$ in the fluid to be treated, to 5% breakthrough, for carbon dioxide removal. A 5% breakthrough refers to the point in the invention process where the $CO_2$ concentration in the effluent fluid stream has reached 5% of the $CO_2$ concentration in the inlet fluid stream.

According to the present invention, the composition can be prepared by simply contacting the oxygen-containing metal compound with the inorganic oxide compound. The contacting can be carried out by any methods known in the art such as, for example, mixing or blending, as long as the oxygen-containing metal compound is well-distributed in the inorganic oxide. The composition can be used in the invention process as it is prepared or can be heated to remove moisture, if present in appreciable concentration.

The rate the fluid is contacted with the composition is not critical but can vary with reaction vessel size. Broadly, the rate of fluid introduction can be about 1 to about 30, preferably about 3 to about 20, and most preferably 5 to 10 WHSV (weight hourly space velocity; g of the fluid per g of the oxygen-containing metal compound per hour). The rate of fluid introduction can also be expressed in total volume of fluid per minute per g of the oxygen-containing metal compound and it is generally in the range from about 13 to about 400 cm$^3$/min-g. The rate often varies as a function of the pressure employed in introducing to fluid which is generally in the range of from about 0 to about 2500 psig, preferably about 0 to about 2000 psig, and most preferably 0 to 1700 psig. In any event, it should be at a rate sufficient to effect efficient contact between the fluid and the composition.

According to the invention, the process can be carried out at a temperature sufficient to effect a substantial removal of the carbon dioxide from the fluid. Generally, the temperature can be in the range of from about 1 to about 200° C., preferably about 1 to about 100° C., and most preferably 1 to 50° C. Generally the time required for $CO_2$ removal in a batch mode is dependent upon the concentration of the carbon dioxide in the fluid, the amount of the composition used, or the amount of the fluid to be treated, or combinations thereof.

The process of the present invention can be carried out in any suitable vessel or device. The choice of a suitable device is a matter of preference to one skilled in the art. The process is also well suited for a continuous process in which the fluid is continuously introduced over a bed of the adsorbent composition under a desired process condition. Once the adsorbent composition approaches saturation with carbon dioxide, to a point of increasing breakthrough of $CO_2$ concentration in the effluent fluid, a new batch of the composition can be used.

The following examples further illustrates the present invention and are not intended to unduly limit the scope of the invention.

EXAMPLE 1

This example illustrates the invention procedure for removing carbon dioxide from an olefin-containing fluid.

The adsorption was carried out using a 3 inch stainless steel tubing having a ⅜ inch inner diameter. The tubing was packed with 2.1 g of sodium hydroxide (20–60 mesh) which had been previously mixed with 2.1 g of silica gel (20–60 mesh). An ethylene stream containing 4555 ppm by volume of carbon dioxide was passed over the adsorbent composition, through the tubing, at a rate of about 200 cubic centimeter per minute at about 25° C. under atmospheric pressure. The effluent stream was monitored for carbon dioxide concentration using a gas chromatograph equipped with $CO_2$ methanation capability and a flame ionization detector. The $CO_2$ was determined with an externally calibrated method. The results are shown in Table I.

TABLE I

Carbon Dioxide Removal from Ethylene Fluid Stream Using NaOH:Silica (1:1) Mixture

| Volume Effluent (liters) | $CO_2$ In Effluent (ppmv) |
|---|---|
| 13.2 | ND* |
| 21.9 | ND |
| 30.9 | ND |
| 39.9 | ND |
| 51.8 | ND |
| 60.8 | ND |
| 69.7 | ND |
| 81.6 | ND |
| 87.6 | 1.4 |
| 100.0 | 417.5 |
| 103.2 | 1079.4 |
| 106.4 | 2208.2 |
| 109.6 | 3105.0 |
| 112.7 | 3921.4 |
| 115.9 | 4429.2 |
| 119.1 | 4533.9 |

Loading at 5% breakthrough (94.3 liters, g $CO_2$ adsorbed/g NaOH) = 42.2%.
Total capacity (g $CO_2$ adsorbed/g NaOH) = 45.6%.
*ND - Not detectable.

The results shown in table I indicate that, with the invention composition as adsorbent, more than 87 liters of ethylene was purified before any appreciable $CO_2$ concentration was detected in the effluent ethylene fluid.

EXAMPLE II

This example shows that a mixture of sodium hydroxide and silica having a weight ratio of 3:1 (NaOH:silica) also serves as a good carbon dioxide adsorbent.

The run was carried out the same as that described in Example I except that the weight ratio of sodium hydroxide to silica was 3:1, i.e., 2 grams of NaOH and 0.67 grams of silica. The results are shown in Table II.

TABLE II

Carbon Dioxide Removal from Ethylene Fluid Stream Using NaOH:Silica (3:1) Mixture

| Volume Effluent (liters) | $CO_2$ In Effluent (ppmv) |
|---|---|
| 11.7 | ND* |
| 20.6 | ND |
| 29.6 | ND |
| 41.4 | ND |
| 50.4 | ND |
| 59.4 | ND |
| 65.4 | 0.7 |
| 80.4 | 25.81 |
| 89.8 | 626.7 |
| 99.0 | 1411.3 |
| 108.0 | 2299.3 |
| 119.9 | 3379.4 |
| 129.0 | 4022.6 |
| 138.0 | 4553.4 |

Loading at 5% breakthrough (84.5 liters, g $CO_2$ adsorbed/g NaOH) = 37.8%.
Total capacity (g $CO_2$ adsorbed/g NaOH) = 48.1%.
*ND - Not detectable.

Similar to the results shown in Table I, Table II shows that, using the invention composition, no $CO_2$ was detected in the effluent ethylene fluid until more than 65 liters of ethylene passed through the invention composition.

EXAMPLE III

This example is a comparative example, showing that, using sodium hydroxide alone as a $CO_2$ absorbent, sodium hydroxide becomes plugged upon exposure to a limited quantity of ethylene fluid.

The run was carried out the same as that described in Example I with the exception that 2 grams of sodium hydroxide was used as $CO_2$ adsorbent. The results shown in Table III indicate that the adsorbent became plugged up with less than 31 liters of ethylene fluid passed through the absorbent.

TABLE III

Carbon Dioxide Removal from Ethylene Using NaOH

| Volume Effluent (liters) | $CO_2$ In Effluent (ppmv) |
|---|---|
| 9.3 | ND* |
| 21.5 | ND |
| 30.8 | 1.5+ |

*ND - Not detectable.
+Reactor plugged and prohibited continuation of experiment.
Loading prior to plugging (g $CO_2$ adsorbed/g NaOH) = 13.8%.

The results shown in the above example clearly demonstrate that the present invention is well adapted to carry out the objects and attain the ends and advantages mentioned as well was those inherent therein. While modifications may be made by those skilled in the art, such modifications are encompassed within the spirit of the present invention as defined by the disclosure and the claims.

That which is claimed is:

1. A process for removing carbon dioxide out of an olefin containing fluid comprising contacting said fluid with a composition wherein said composition consists essentially of (1) an oxygen-containing metal compound selected from the group consisting of sodium hydroxide, potassium hydroxide, magnesium hydroxide and combinations of two or more thereof, and (2) silica; said fluid comprises at least one $C_2$–$C_4$ olefin and carbon dioxide; said fluid is selected from the group consisting of gas, liquid, and combinations thereof; said process is carried out under conditions sufficient to substantially remove said carbon dioxide from said fluid; and the weight ratio of said oxygen-containing metal compound to said silica is in the range of from about 0.1:1 to about 10:1.

2. A process according to claim 1 wherein said olefin is ethylene.

3. A process according to claim 1 wherein said olefin is propylene.

4. A process according to claim 1 wherein said oxygen-containing metal compound is sodium hydroxide.

5. A process according to claim 1 wherein the weight ratio of said carbon dioxide to said olefin is in the range of from about 0.000001:1 to about 0.1:1.

6. A process according to claim 1 wherein the weight ratio of said carbon dioxide to said olefin is in the range of from 0.000001:1 to 0.01:1.

7. A process according to claim 1 wherein the weight ratio of said oxygen-containing metal compound to said silica is in the range of from 0.15:1 to 4:1.

8. A process according to claim 1 wherein the amount of said oxygen-containing metal compound is in the range of from about 1 to about 20 g per g of $CO_2$ in said fluid which is contacted with said oxygen-containing metal compound.

9. A process according to claim 1 wherein the amount of said oxygen-containing metal compound is in the range of from about 2 to about 10 g per g of $CO_2$ in said fluid which is contacted with said oxygen-containing metal compound.

10. A process according to claim 1 wherein the amount of said oxygen-containing metal compound is in the range of from 2 to 5 g per g of $CO_2$ in said fluid which is contacted with said oxygen-containing metal compound.

11. A process according to claim 1 wherein said process is carried out at a temperature in the range of from about 1° C. to about 200° C.

12. A process according to claim 1 wherein said process is carried out at a temperature in the range of from 1° C. to 50° C.

13. A process according to claim 1 wherein said process is carried out under a pressure in the range of from about 0 psig to about 2500 psig.

14. A process according to claim 1 wherein said process is carried out under a process of from 0 psig to 1700 psig.

15. A process according to claim 1 wherein said oxygen-containing metal compound is potassium hydroxide.

16. A process according to claim 1 wherein said oxygen-containing metal compound is magnesium hydroxide.

17. A process for removing carbon dioxide out of an olefin containing a fluid comprising contacting said fluid with a composition under conditions sufficient to substantially remove said carbon dioxide from said fluid stream wherein said fluid stream comprises at least one $C_2$–$C_4$ olefin and carbon dioxide; said composition consists essentially of (1) an oxygen-containing metal compound chosen from the group consisting of sodium hydroxide, potassium hydroxide and magnesium hydroxide and (2) silica; the weight ratio of said carbon dioxide to said fluid is in the range of from about 0.000001:1 to about 0.1:1; the weight ratio of said oxygen containing metal compound to said silica is in the range of from about 0.1:1 to about 10:1; and the amount of said oxygen containing metal compound is in the range of from about 1 g to about 20 g per g of $CO_2$ in said fluid to be contacted.

18. A process according to claim 17 wherein said olefin is chosen from the group consisting of ethylene, propylene and mixtures thereof; said oxygen-containing metal compound is sodium hydroxide; the weight ratio of said carbon dioxide to said fluid is in the range of from 0.00001:1 to 0.01:1; the weight ratio of said oxygen-containing metal compound to said inorganic oxide is in the range of from 0.15:1 to 4:1; and the amount of said oxygen-containing metal compound is in the range of from 2 g to 5 g per g of $CO_2$ in said fluid to be contacted.

19. A process according to claim 17 wherein said olefin is chosen from the group consisting of ethylene, propylene and mixtures thereof; said oxygen-containing metal compound is potassium hydroxide; the weight ratio of said carbon dioxide to said fluid is in the range of from 0.00001:1 to 0.01:1; the weight ratio of said oxygen-containing metal compound to said silica is in the range of from 0.15:1 to 4:1; and the amount of said oxygen-containing metal compound is in the range of from 2 g to 5 g per g of $CO_2$ in said fluid stream to be contacted.

20. A process according to claim 17 wherein said olefin is chosen from the group consisting of ethylene, propylene and mixtures thereof; said oxygen-containing metal compound is magnesium hydroxide; the weight ratio of said carbon dioxide to said fluid is in the range of from 0.00001:1 to 0.01:1; the weight ratio of said oxygen-containing metal compound to said silica is in the range of from 0.15:1 to 4:1; and the amount of said oxygen-containing metal compound is in the range of from 2 g to 5 g per g of $CO_2$ in said fluid, to be contacted.

21. A process for removing carbon dioxide from a fluid comprises contacting said fluid with a composition under conditions sufficient to remove said carbon dioxide from said fluid wherein said fluid comprises carbon dioxide and an olefin selected from the group consisting of ethylene, propylene, and combinations thereof; said composition consists essentially of sodium hydroxide silica; the weight ratio of said carbon dioxide to said fluid is in the range of from 0.000001:1 to 0.01:1; the weight ratio of said sodium hydroxide to said silica is in the range of from 0.015:1 to 4:1.; and the amount of said sodium hydroxide is in the range of from 2 g to 5 g per g of $CO_2$ in said fluid to be contacted.

22. A process according to claim 21 wherein said olefin is ethylene.

23. A process according to claim 21 wherein said olefin is propylene.

* * * * *